(12) United States Patent
Campbell et al.

(10) Patent No.: US 6,277,479 B1
(45) Date of Patent: Aug. 21, 2001

(54) MICROPOROUS FILMS HAVING ZONED BREATHABILITY

(75) Inventors: Stephen Michael Campbell, Winneconne, WI (US); Howard Martin Welch, Woodstock, GA (US); Larry Ned Barnett, Jr., Church Hill, TN (US); Carol Ann Blaney, Roswell, GA (US); David Arthur Fell, Neenah, IL (US); Sarah Jane Marie Freiburger, Kaukauna, WI (US); William Bela Haffner, Kennesaw, GA (US); Marianne Keevill Leick, Appleton, WI (US); Ann Louise McCormack, Cumming; Douglas H. Tulley, Jr., Atlanta, both of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/164,026

(22) Filed: Sep. 30, 1998

Related U.S. Application Data

(60) Provisional application No. 60/068,353, filed on Dec. 19, 1997.

(51) Int. Cl.$^7$ .................................................. B32B 3/26
(52) U.S. Cl. .................. 428/213; 428/218; 428/315.7; 428/316.6; 428/319.7; 428/913; 442/370
(58) Field of Search .................................. 428/213, 218, 428/315.7, 316.6, 319.7, 913; 442/370

(56) References Cited

U.S. PATENT DOCUMENTS

| | | | |
|---|---|---|---|
| Re. 35,206 | 4/1996 | Hassenboehler, Jr. et al. | 55/528 |
| D. 390,708 | 2/1998 | Brown | D5/61 |
| 3,844,865 | 10/1974 | Elton et al. | 156/229 |
| 3,855,046 | 12/1974 | Hansen et al. | 161/150 |
| 4,041,203 | 8/1977 | Brock et al. | 428/157 |
| 4,116,892 | 9/1978 | Schwarz | 521/62 |
| 4,533,510 | 8/1985 | Nissel . | |

(List continued on next page.)

FOREIGN PATENT DOCUMENTS

| | | |
|---|---|---|
| 0 515 501 | 6/1994 | (EP) . |
| 0 797 968 | 3/1996 | (EP) . |
| 0 319 222 | 6/1999 | (EP) . |
| 2293573 | 4/1996 | (GB) . |
| 2311249 | 9/1997 | (GB) . |
| 91/03367 | 3/1991 | (WO) . |
| 95/09261 | 4/1995 | (WO) . |
| 96/19346 | 6/1996 | (WO) . |
| 97/24482 | 7/1997 | (WO) . |
| 97/36561 | 10/1997 | (WO) . |
| 97/48358 | 12/1997 | (WO) . |
| 98/27920 | 7/1998 | (WO) . |
| 98/29246 | 7/1998 | (WO) . |
| 98/29479 | 7/1998 | (WO) . |
| 98/29480 | 7/1998 | (WO) . |
| 00/10500 | 3/2000 | (WO) . |

OTHER PUBLICATIONS

Abstract of JP 63–066241 (Mar. 98).

Primary Examiner—Blaine Copenheaver
(74) Attorney, Agent, or Firm—Douglas H. Tulley; James B. Robinson

(57) ABSTRACT

Breathable microporous films are provided having controlled regional breathability with thick high WVTR regions and thinner low WVTR regions. The zoned breathable microporous films can be made by selectively applying heat and/or pressure to specific regions the microporous film such as by feeding a microporous film through a pair of heated nip rollers with one of the rolls having a raised surface area or by applying a focused stream of hot air. Monolayer microporous films and multilayer films having at least one microporous layer can be treated to impart zoned breathability to the film.

24 Claims, 7 Drawing Sheets

U.S. PATENT DOCUMENTS

| | | | |
|---|---|---|---|
| 4,563,229 | 1/1986 | Sorez | 156/64 |
| 4,713,069 | 12/1987 | Wang et al. | 604/378 |
| 4,777,073 | 10/1988 | Sheth | 428/155 |
| 4,854,984 | 8/1989 | Ball et al. | 156/73.5 |
| 4,867,881 | 9/1989 | Kinzer | 210/490 |
| 4,877,679 | 10/1989 | Leatherman et al. | 428/224 |
| 5,120,594 | 6/1992 | Mrozinski | 428/195 |
| 5,188,885 | 2/1993 | Timmons et al. | 428/198 |
| 5,238,623 | 8/1993 | Mrozinski | 264/48 |
| 5,272,236 | 12/1993 | Lai et al. | 526/348.5 |
| 5,308,691 | 5/1994 | Lim et al. | 428/286 |
| 5,331,047 | 7/1994 | Giacobbe | 525/88 |
| 5,364,381 | 11/1994 | Soga et al. | 604/366 |
| 5,409,761 | 4/1995 | Langley | 428/198 |
| 5,424,025 | 6/1995 | Hanschen et al. | 264/288.8 |
| 5,472,775 | 12/1995 | Obijeski et al. | 428/220 |
| 5,560,974 | 10/1996 | Langley | 428/198 |
| 5,571,096 | 11/1996 | Dobrin et al. | 604/383 |
| 5,616,385 | 4/1997 | Rothrum et al. | |
| 5,651,853 | 7/1997 | Wrigley et al. | 156/290 |
| 5,665,083 | 9/1997 | Igaue et al. | 604/370 |
| 5,673,433 | 10/1997 | Rothrum | 2/46 |
| 5,688,476 | 11/1997 | Bourne et al. | 422/294 |
| 5,695,868 | 12/1997 | McCormack | 428/283 |
| 5,714,107 | 2/1998 | Levy et al. | 264/289.3 |
| 5,810,797 | 9/1998 | Menard et al. | 604/378 |
| 5,865,823 | 2/1999 | Curro | |

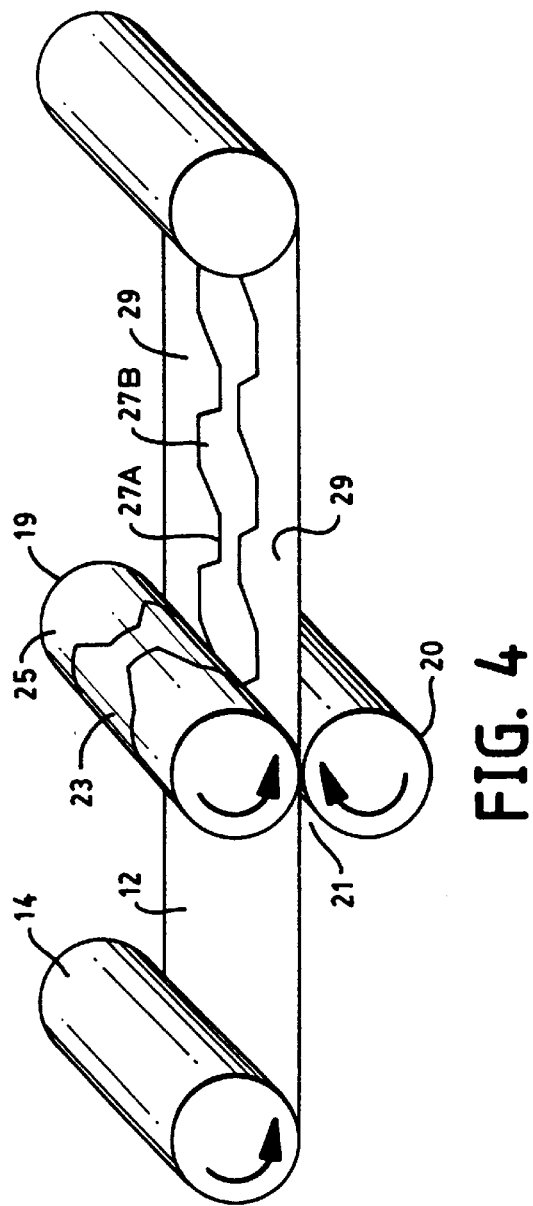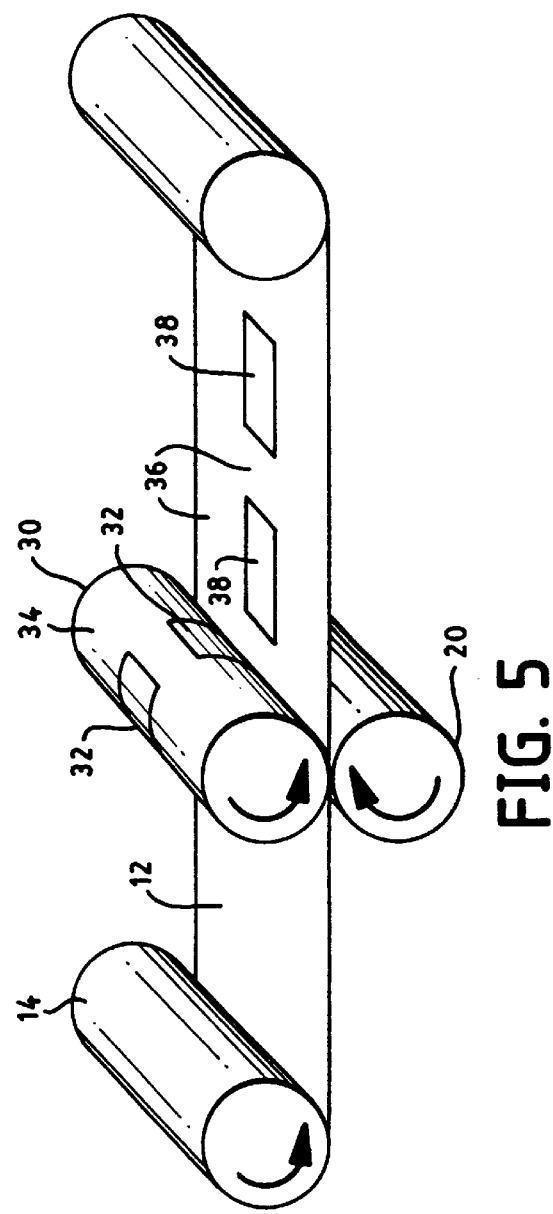

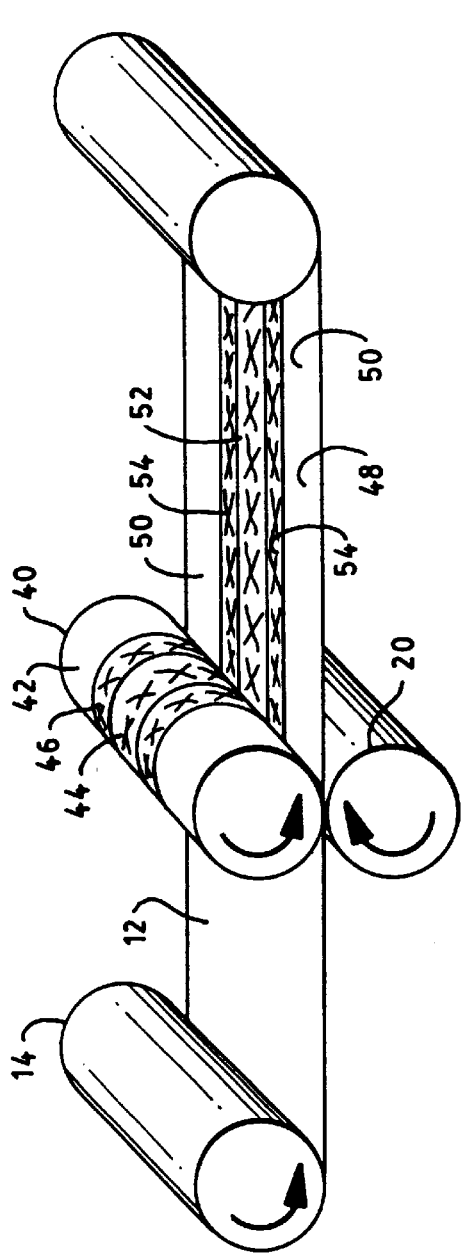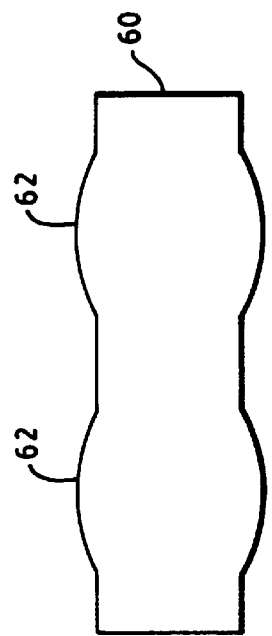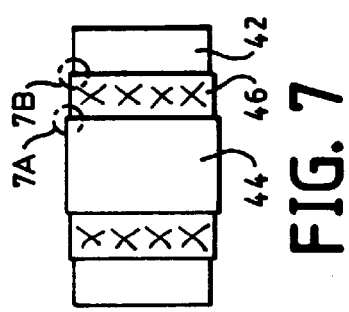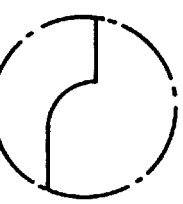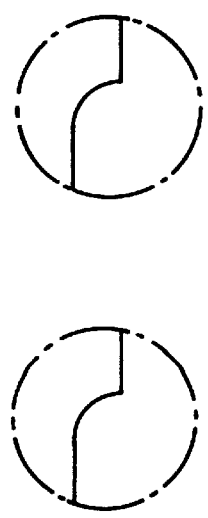

MICROPOROUS FILMS HAVING ZONED BREATHABILITY

This application claim benefit to Provisional Application Ser. No. 60/068,363 filed Dec. 19, 1997.

FIELD OF THE INVENTION

The present invention relates to breathable microporous films. More particularly, the present invention relates to breathable microporous films having zoned breathability and methods of making the same.

BACKGROUND OF THE INVENTION

Microporous films are "breathable" barriers in the sense that the film acts as a barrier to liquids and particulate matter but allows water vapor and air to pass therethrough. In addition, by achieving and maintaining high breathability it is possible to provide an article that is more comfortable to wear since the migration of water vapor through the fabric helps reduce and/or limit discomfort resulting from excess moisture trapped against the skin. Thus, such an article can potentially contribute to an overall improved skin wellness.

Accordingly, microporous films have become an important article of commerce, finding a wide variety of applications. For example, microporous films have been used as outer covers for personal care products such as diapers, training pants, incontinence garments, feminine hygiene products and the like. In addition, microporous films have likewise found use in protective apparel and infection control products such as surgical gowns, surgical drapes, protective workwear, wound dressings and bandages. Often microporous films are utilized as multilayer laminates in such applications. The films can provide the desired barrier properties to the article while other materials laminated thereto can provide additional characteristics such as strength, abrasion resistance and/or good hand. For example, fibrous webs such as nonwoven fabrics allow the laminate to retain its breathability and can provide additional strength as well as an article having a cloth-like feel. Thus, microporous film laminates can be used in a variety of applications including, for example, those described above.

Although the breathability provided by microporous films and/or laminates thereof is advantageous in many articles, there exist some situations where high breathability can be undesirable. For example, in personal care articles such as diapers or incontinence garments the breathable barrier and absorbent core generally work together to retain bodily fluids discharged into the garment. However, when fluid is retained within the absorbent core, significantly higher levels of water vapor begin to pass through the breathable barrier. The increased levels of water vapor passing through the outer cover can form condensate on the outer surface of the garment. The condensate is simply water but can be perceived by the wearer as leakage. In addition, the condensate can create a damp uncomfortable feel to the outer portion of the garment which is unpleasant for those handling the article. It is believed that the skin wellness and/or improved comfort benefits of breathable outer covers are often not achieved at areas directly adjacent to the portion of the absorbent core which retains considerable amounts of liquid (e.g. typically those areas of the central or crotch region of the garment). Providing a breathable barrier which has less or limited breathability in such regions, while providing good breathability in the remaining regions, would provide a garment with excellent wearer comfort yet which limits the potential for outer cover dampness. Thus, a breathable barrier that provides either zoned or controlled regional breathability is highly desirable.

Therefore, there exists a need for a breathable microporous film having regions with varied levels of breathability. In addition, there exists a need for such films which retain the desired barrier properties and which are capable of lamination to additional materials. Further, there exists a need for methods of making such films and in particular methods of reliably obtaining the desired levels of breathability in distinct regions of a film.

SUMMARY OF THE INVENTION

The aforesaid needs are fulfilled and the problems experienced by those skilled in the art overcome by the film of present invention which, in one aspect, comprises a first microporous region having a thickness less than 50 $\mu$ and a WVTR of at least 800 g/m$^2$/24 hours and a second region having a thickness substantially equal to or less than that of the first region wherein the WVTR of the second region is at least 15% less than the WVTR of the first region. Desirably the second region has decreased porosity relative to that of the first region. Despite the existence of variations in film structure, the film can have a hydrohead of at least about 50 mbar. The second region desirably has minimum dimensions of 3 cm by 5 cm and still more desirably comprises from about 5% to about 75% of the area of said film. In one embodiment, the first region can have a WVTR in excess of about 2500 g/m$^2$/24 hours and the second region a WVTR less than about 1500 g/m$^2$/24 hours. Additionally, the second region can have a thickness less than about 95% of the thickness of the first region. Further, the film can comprise a third region having a WVTR intermediate to that of the first and second regions. The film can be a monolayer film or part of a multilayer film structure and can also be laminated with one or more additional materials as desired.

In a further aspect of the invention, methods of making films having regions of varied breathability are provided and can comprise providing a microporous film having a hydrohead of at least 50 mbars and a WVTR of at least 800 g/m$^2$/24 hours and then selectively applying heat and/or pressure to a portion of said film thereby creating first and second regions therein. The porosity and the WVTR is decreased within the second region of the microporous film, i.e. the region to which heat and/or pressure has been selectively applied, relative to the WVTR and porosity of the first region. In one embodiment, the film can be heated prior to and/or simultaneously with application of pressure. The second region can have a minimum dimensions of at least 3 cm by 5 cm and desirably the second region comprises from about 5% to about 75% of the area of said film. In a particular embodiment, pressure is selectively applied to the microporous film by a pair of rollers wherein at least one of the rollers is a patterned roller having a raised surface. Optionally, one or both of the rollers can be heated. Monolayer or multilayer films having at least one microporous layer can be utilized in conjunction with the methods of the present invention.

In still a further aspect of the invention, methods of making film laminates having varied regional breathability are provided and can comprise providing a breathable thermoplastic polymer microporous film having a WVTR of at least 800 g/m$^2$/24 hours and a hydrohead of at least 50 mbars and bonding the breathable film to a breathable fibrous material thereby forming a multilayer laminate. The fibrous material can comprise a resilient polymeric material having a melting point at least 10° C. greater than the thermoplastic polymer comprising said film. A selected region of the microporous film can then be treated with sufficient energy wherein the porosity within that region of the microporous film is decreased a desired amount. In a particular embodiment, a selected region of the film laminate can be treated to reduce its WVTR by selectively exposing the region to sufficient heat, such as by focused hot air, capable of causing a significant melt fraction in the film polymer. With the onset of a significant melt fraction the porosity of the film can be decreased, i.e. the density increased, within the selected region of the film.

DEFINITIONS

As used herein the term "nonwoven" fabric or web means a web having a structure of individual fibers or threads which are interlaid, but not in an identifiable manner as in a knitted or woven fabric. Nonwoven fabrics or webs have been formed by many processes such as for example, meltblowing processes, spunbonding processes, hydroentangling, air-laid and bonded carded web processes.

As used herein the term "spunbond fibers" refers to small diameter fibers of substantially molecularly oriented polymeric material. Spunbond fibers are generally formed by extruding molten thermoplastic material as filaments from a plurality of fine, usually circular capillaries of a spinneret with the diameter of the extruded filaments then being rapidly reduced such as, for example, as described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, U.S. Pat. No. 5,382,400 to Pike et al.; U.S. Pat. No. 5,795,926 to Pike et al.; and in commonly assigned U.S. patent application No. 08/756,426 filed Nov. 26, 1996 (pending) to Marmon et al. Spunbond fibers are generally not tacky when they are deposited onto a collecting surface and are generally continuous.

As used herein the term "meltblown fibers" means fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al., and U.S. Pat. No. 5,271,883 to Timmons et al. Meltblown fibers may be continuous or discontinuous, are generally smaller than 10 microns in average diameter, and are generally tacky when deposited onto a collecting surface.

As used herein "multilayer nonwoven laminate" means a laminate of two or more nonwoven layers such as, for example, wherein some of the layers are spunbond and some meltblown; e.g. a spunbond/meltblown/spunbond (SMS) laminate. Examples of multilayer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein, the term "machine direction" or MD means the direction of the fabric in the direction in which it is produced. The term "cross machine direction" or CD means the direction of the fabric substantially perpendicular to the MD.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries.

As used herein, "ultrasonic bonding" means a process performed, for example, by passing the fabric between a sonic horn and anvil roll as illustrated in U.S. Pat. No. 4,374,888 to Bornslaeger.

As used herein "point bonding" means bonding one or more layers of fabric at numerous small, discrete bond points. For example, thermal point bonding generally involves passing one or more layers to be bonded between heated rolls such as, for example an engraved patterned roll and a flat calender roll. The engraved roll is patterned in some way so that the entire fabric is not bonded over its entire surface, and the anvil roll is usually flat. As a result, various patterns for engraved rolls have been developed for functional as well as aesthetic reasons. One example of a pattern has points and is the Hansen Pennings or "H&P" pattern with about a 30% bond area when new and with about 200 bonds/square inch as taught in U.S. Pat. No. 3,855,046 to Hansen et al.

As used herein, the term "barrier" means a film, laminate or other fabric which is relatively impermeable to the transmission of liquids and which has a hydrohead of at least about 50 mbar. Hydrohead is a measure of the liquid barrier properties of a fabric measured in millibars (mbar) as described herein below. However, it should be noted that in many applications of barrier fabrics, it may be desirable that they have a hydrohead value greater than about 80 mbar, 150 mbar or even 200 mbar.

As used herein, the term "breathability" refers to the water vapor transmission rate (WVTR) of an area of fabric which is measured in grams of water per square meter per day ($g/m^2/24$ hours). The WVTR of a fabric is the water vapor transmission rate which, in one aspect, gives an indication of how comfortable a fabric would be to wear. WVTR can be measured as indicated below.

As used herein the term "monocomponent" fiber refers to a fiber formed from one or more extruders using only one polymer. This is not meant to exclude fibers formed from one polymer to which additives have been added. As used herein the term "multicomponent fibers" refers to fibers which have been formed from at least two polymers extruded from separate extruders but spun together to form one fiber. Multicomponent fibers are also sometimes referred to as conjugate or bicomponent fibers. The polymers of a multicomponent fiber are arranged in substantially constantly positioned distinct zones across the cross-section of the fiber and extend continuously along the length of the fiber. The configuration of such a fiber may be, for example, a sheath/core arrangement wherein one polymer is surrounded by another or may be a side by side arrangement, a pie arrangement or an "islands-in-the-sea" type arrangement. Multicomponent fibers are taught in U.S. Pat. No. 5,108,820 to Kaneko et al., U.S. Pat. No. 4,795,668 to Krueger et al. and U.S. Pat. No. 5,336,552 to Strack et al.

Conjugate fibers and methods of making them are also taught in U.S. Pat. No. 5,382,400 to Pike et al. and may be used to produce crimp in the fibers by using the differential crystallization properties of the two (or more) polymers. The fibers may also have various shapes such as those described in U.S. Pat. Nos. 5,277,976 to Hogle et al., U.S. Pat. No. 5,466,410 to Hills and 5,069,970 and 5,057,368 to Largman et al.

As used herein the term "blend" means a mixture of two or more polymers while the term "alloy" means a sub-class of blends wherein the components are immiscible but have been compatibilized.

As used herein the term "biconstituent fibers" or "multi-constituent" refers to fibers which have been formed from at least two polymers extruded from the same extruder as a blend. The term "blend" is defined above. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are discussed in U.S. Pat. No. 5,294,482 to Gessner and in the textbook *Polymer Blends and Composites* by John A. Manson and Leslie H. Sperling, copyright 1976 by Plenum Press, a division of Plenum Publishing Corporation of New York, ISBN 0-306-30831-2, at pages 273 through 277.

As used herein, the term "scrim" means a lightweight fabric used as a backing material. Scrims are often used as the base fabric for coated or laminated products.

As used herein, the term "garment" means any type of non-medically oriented apparel which may be worn. This includes industrial workwear and coveralls, undergarments, pants, shirts, jackets, gloves, socks, and the like.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets and the like.

As used herein, the term "personal care product" means personal hygiene oriented items such as diapers, training pants, absorbent underpants, adult incontinence products, feminine hygiene products, and the like.

As used herein, the term "protective cover" means a cover for vehicles such as cars, trucks, boats, airplanes, motorcycles, bicycles, golf carts, etc., covers for equipment often left outdoors like grills, yard and garden equipment (mowers, rototillers, etc.) and lawn furniture, as well as floor coverings, table cloths, picnic area covers, tents, tarpaulins and the like.

BRIEF DESCRIPTION OF THE DRAWINGS

FIG. 4 is a schematic representation of an exemplary nip roll assembly suitable for practicing the present invention and a zone treated film made therefrom.

FIG. 5 is a schematic representation of an exemplary nip roll assembly suitable for use in practicing the present invention and a zone treated film made therefrom.

FIG. 6 is a schematic representation of an exemplary nip roll assembly suitable for use in practicing the present invention and a zone treated film made therefrom.

FIG. 7 is a cross-sectional representation of an exemplary patterned roll suitable for use in practicing the present invention.

FIG. 8 is a cross-sectional representation of an exemplary patterned roll suitable for use in practicing the present invention.

DETAILED DESCRIPTION OF THE INVENTION

Figure 1:
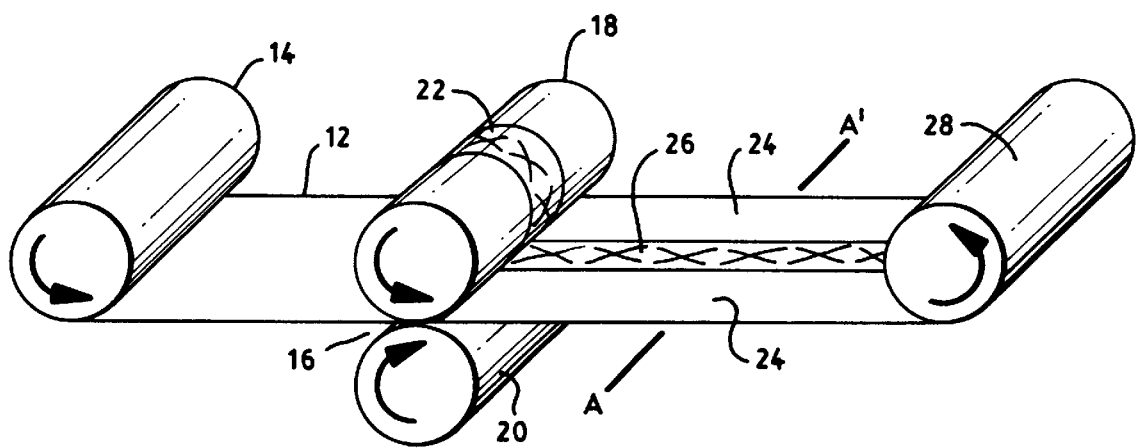
FIG. 1 is a schematic representation of an exemplary nip roll assembly suitable for se in practicing the present invention and a zone treated film made therefrom.

A breathable microporous film can be treated, in accord with the present invention, to create a breathable film having regions of varied breathability. In reference to FIG. 1, microporous film 12 is unwound from supply roll 14 and fed into nip 16 created by first and second nip rolls 18 and 20. The first nip roll 18 can have a patterned surface such as raised surface 22 whereby the film entering nip 16 adjacent raised surface 22 experiences compacting pressure. The second nip roll 20 can be a flat (i.e. unpatterned) or patterned roll although desirably second nip roll 20 comprises an unpatterned roll. The microporous film 12 is desirably heated and can be heated prior to entering nip 16 and/or upon entering the nip roll assembly. Desirably the film is heated by using one or more heated rolls. The heat and/or pressure applied to the microporous film reduces the size and/or number of pores within the microporous film thereby reducing the breathability or WVTR of the film in the treated areas. The degree to which the porosity and the corresponding WVTR is decreased within the selectively treated regions will vary with the amount of heat and/or pressure applied thereto. Thus, a breathable microporous film can be made having regions of controlled, varied breathability. Still in reference to FIG. 1, a microporous film is created having first breathable regions 24 and second regions 26 wherein the breathability or WVTR of the second regions 26 are lower than that of the first region 24. The treated film can then be wound on a winder roll 28 or further processed and/or converted as desired.

Suitable microporous films for practicing the present invention include breathable microporous films having a WVTR of at least 800 g/m$^2$/24 hours, and more desirably having a WVTR in excess of 1500 g/m$^2$/day, 2500 g/m$^2$/24 hours or 3500 g/m$^2$/24 hours. Desirably, the breathable microporous film substrate has a WVTR between about 2000 g/m$^2$/24 hours and about 7000 g/m$^2$/24 hours, however, microporous films with WVTRs above 7000 g/m$^2$/24 hours are also suitable for use with the present invention. The breathable microporous films preferably have a film thickness less than about 60 $\mu$ and desirably have a thickness between about 10 $\mu$ and about 35 $\mu$. Thin breathable microporous film can be formed by any one of various methods known in the art. Examples of microporous films suitable for use with the present invention include, but are not limited to, those described in the following references: U.S. Pat. No. 4,777,073 to Sheth; and U.S. Pat. No. 4,867,881 to Kinzer; U.S. Pat. No. 5,695,868 to McCormack; U.S. patent application Ser. No. 08/742,435 filed Feb. 2, 1998 to McCormack et al.; U.S. patent application Ser. No. 08/882,712 filed Jun. 25, 1997 to McCormack et al.; WO 95/16562 filed Jun. 22, 1995 to McCormack; WO 96/19346 filed Jun. 27, 1996 to McCormack et al.; U.S. patent application Ser. No. 08/722,726 filed Oct. 1, 1996 to McCormack et al.; U.S. patent application Ser. No. 08/883,164 filed Jun. 25, 1997 to McCormack et al.; U.S. patent application Ser. No. 08/843,147 filed Apr. 25, 1997 to Gwaltney et al.; U.S. patent application Ser. No. 08/929,562 filed Sep. 15, 1997 to Haffner et al.; and U.S. patent application Ser. No. 09/122,326 filed Jul. 24, 1998, now abandoned, to Shawver et al; the entire contents of the aforesaid references are incorporated herein by reference.

A preferred breathable microporous film can comprise a stretched filled-film which includes a thermoplastic polymer and filler. These and other components can be mixed together, heated and then extruded into a monolayer or multilayer film. The filled film may be made by any one of a variety of film forming processes known in the art such as, for example, by using either cast or blown film equipment. The thermoplastic polymer and filler can be stretched in at least one direction, thereby reducing the film gauge or thickness and creating a network of micropores within the film of a size and frequency to achieve the desired level of breathability. Such films, prior to stretching, desirably have a basis weight of less than about 100 g/m$^2$ and even more desirably less than about 60 g/m$^2$. Upon stretching the multilayer film desirably has a basis weight of less than about 60 g/m$^2$ and even more desirably between about 15 and 35 g/m$^2$. Suitable films can also include multilayer films having at least one microporous layer such as, for example, those described in PCT Publication WO 96/19346 and U.S. patent application No. 08/882,712, pending, the entire content of which is incorporated herein by reference.

Mechanically deformable polymer films are believed to be suitable for use with the present invention (e.g. soft rubbers). Thus, the microporous films can comprise known film forming polymers which are, by mechanical and/or thermal treatment, permanently deformable. Desirably, however, the microporous film can be made from a thermoplastic polymer. Blends and/or copolymers of thermoplastic polymers are likewise suitable for use with the present invention. Various film forming polymers suitable for use with the present invention, alone or in combination with other polymers, include ethylene vinyl acetate, ethylene ethyl acrylate, ethylene acrylic acid, ethylene methyl acrylate, ethylene normal butyl acrylate, polyester, polyethylene terephthalate, polyamides (e.g. nylon), ethylene vinyl alcohol, polystyrene, polyurethane, polybutylene, and polybutylene terephthalate. However, polyolefin polymers are preferred such as, for example, polymers of ethylene and propylene as well as copolymers, terpolymers and blends thereof; examples include, but are not limited to, linear low density polyethylene (LLDPE) and ethylene-propylene copolymer blends. The microporous films can comprise elastic or inelastic polymers. With thermoplastic polymer microporous films sufficient energy, e.g. heat and/or pressure, should be imparted to adequately stabilize and/or set the treated region of the film.

Once the breathable microporous film has been formed, that is the fine pore network has been created within and/or across the film, the microporous film can be treated to impart zoned or controlled regional breathability thereto. The microporous film can be made in-line or made previously and unwound from a supply roll. Selected regions of the microporous film are treated with sufficient localized energy (e.g. heat and/or pressure) to increase the film density and reduce the number and/or size of pores therein. This treatment selectively reduces and/or substantially eliminates the breathability previously imparted to the film in that region. For example, the microporous film can be passed through a pair of patterned nip rollers which apply a pre-determined amount of pressure to reduce the pore structure to a desired degree. The degree of pressure applied by the nip rolls will vary with respect to the type of polymer comprising the microporous film, the thickness of the microporous film, the temperature of the film and the level of breathability desired in the zone-treated regions.

Desirably at least one of the nip rolls is patterned so as to have a raised surface. The patterns on the rollers can be varied so as to create the zoned breathability in the film as desired. However, small discrete raised projections on the nip roll, such as those utilized in thermal point bonding described herein above having numerous pins per inch, can create a film with degraded barrier properties and/or strength. Thus, the raised surface(s) of the roller(s) is such that the corresponding treated regions of the film desirably extend at least 3 cm in both the CD and MD and more desirably at least 5 cm×5 cm in the CD and MD. Treating larger regions results in a film having good tensile strength and hydrohead values despite the variation in film thickness and/or porosity. The treated regions having comparatively lower breathability and preferably comprise substantially uniform regions. As used herein with reference to the treated regions of the film, the term "substantially uniform" means a continuous region without discrete regions of significantly greater thickness. Further, the raised surface(s) can extend at least 10 cm in either the CD or MD direction. In a further aspect of the invention, the treated regions desirably comprise from about 5% to about 90% of the area of the film. In a particular embodiment of the present invention the treated regions can comprise from about 5% to about 75% of the area of the film and more desirably comprise from about 15% to about 60% of the area of the film. Still more desirably, the treated regions can comprise a single continuous, localized area comprising 5% to about 75% of the area of the film. In a further embodiment, the treated region can have areas therein of intermediate and low breathability or have discrete treated regions of intermediate and low breathability. The regions of low and intermediate breathability desirably form a single continuous area and which, in one aspect, can be disposed about the central portion of the film. However, the treated regions can comprise two or more discrete or non-contiguous regions.

Figure 3:
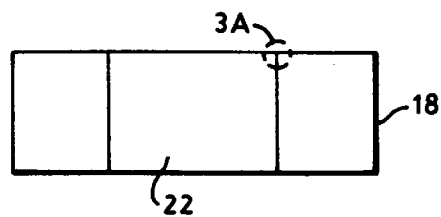
FIG. 3 is a cross-sectional representation of a exemplary patterned roll suitable for use in practicing the present invention.
Figure 3A:
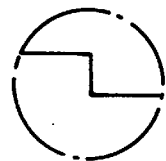

In one embodiment of the present invention, the patterned nip roll can have a raised surface which is continuous. As an example, raised surface 22 can extend around the circumference of a roll such as first nip roll 18 shown in FIGS. 1 and 3. First nip roll 18 having raised surface 22 is shown in FIG. 3 with an enlarged view of the raised surface edge. The raised surface or surfaces can have a squared off edge although it is believed advantageous to employ a rounded or tapered edge along the raised surface of the nip roll. Each of the nip rolls desirably has a hard surface, such as steel rolls, although other materials are believed suitable with the present invention. As an example, it is believed that a rubber coated roll may be advantageous when used in connection with a patterned steel roll. In a further aspect, the patterned roll can have shims along the edge of the patterned roll at substantially the same height of the raised surface to stabilize the rolls and/or improve processing of the film. Desirably the film is of a size, and fed into the nip, such that it does not pass under the shims.

The location of the raised surface(s) can be placed upon the patterned nip roll to treat the microporous film in the desired locations. For example, a patterned roll having a continuous raised surface about the center of the roll can be used to create a zoned breathability microporous film, such as shown in reference to FIG. 1, having highly breathable regions 24 adjacent the opposed edges of the film with central region 26 of reduced breathability therebetween. The reduced breathability region 26 can extend continuously in the machine direction of the microporous film. In a further aspect of the invention, when using a continuous raised surface that extends around the entire circumference of a given length of the roll, the nip pressure can be varied in order to further modify the breathability of the corresponding region of the film. For example, the hydraulic pressure on the rollers could be oscillated in order to achieve varied levels of breathability extending in the machine direction.

In a further aspect of the invention, the raised surface or surfaces can be shaped to create correspondingly shaped regional breathability to the microporous film. In reference to FIG. 4, patterned roll 19 can have raised surface 23 and lower surface 25. Microporous film 12 is fed through nip 21 created by rolls 19, 20 thereby creating a film having first region 29 and second region 27A wherein first region 29 has a higher WVTR than second region 27A. Further, it is believed that continuous region 27 itself will have varied levels of breathability. Narrow sections, second region 27A, will have a lower WVTR than wide sections, third region 27B. It follows that the force per square inch experienced by microporous film 12 will be greater in the narrower sections thereby causing a greater decrease in film breathability in those areas.

In still a further aspect of the invention, the raised surface can be discontinuous in the sense that the raised surface extends around only a portion of the rolls circumference. In reference to FIG. 5, patterned roll 30 has raised surface 32 and lower surface 34 wherein raised surface 32 extends around less than the entire periphery of roll 30. Treatment of a microporous film with such a roll will create first region 36 and second regions 38 whereby first region 36 has greater breathability than second regions 38. Further, second regions 38 will be separated by portions of first region 36 in the machine direction.

As a further example, a patterned roll can have multiple stepped raised surfaces to create a breathability gradient across the CD of the film. In reference to FIGS. 6 and 7, patterned roll 40 has first surface 42, a second surface 44 and a third surface 46 wherein second surface 44 and third surface 46 are raised surfaces relative to first surface 42. Further, third surface 46 can be disposed between first and second surfaces 42, 44 having an intermediate height relative to the adjacent surfaces. The resulting zoned breathable film 48 will have first region 50 of high breathability, second region 52 of low breathability and third region 54 of intermediate breathability. In a further aspect of the invention and in reference to FIG. 8, patterned roll 60 can utilize a crowned or rounded roll, having raised surfaces 62 while having a more regular surface relative to a stepped patterned roll such as discussed in reference to FIG. 3. A film treated in accord with such a patterned roller will have regions of varied breathability with a breathability gradient across the CD of the film as opposed to more distinctly delineated regions of breathability.

In regard to the height of the raised surfaces of the roll(s), this height will vary with respect to the thickness of the untreated microporous film, the level of breathability desired and the hardness of the nip rolls. Desirably the raised surface of the nip has a height of at least 10 microns and more desirably has a height of at least about half the thickness of the untreated film and less than about 1 mm.

Additional energy such as thermal energy can be applied to the film in combination with mechanical compacting pressure. The particular combination of pressure and heat applied to the film will vary with regard the particular polymers involved and the desired characteristics of the treated films. Generally speaking, at equivalent pressures, films heated to higher temperatures experience a greater decrease in porosity and/or thickness. Further, it has been found that within limits recognized by those skilled in the art, CD strength is improved by heating the film to a higher degree. Desirably, sufficient thermal energy is applied to heat the film to about the polymer softening point and it is further desirable that the film not be heated to or above its melting point. However, although use of relatively higher film temperatures are believed suitable for use with the present invention, it is believed that at such temperatures it will be difficult to reliably achieve a controlled or desired level of film breathability. The general relationship between nip pressure, film temperature and impact on film WVTR for thermoplastic polymers is further exemplified in the examples set forth below.

Figure 2:
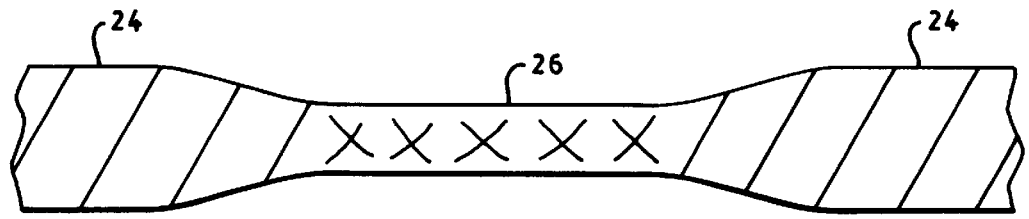
FIG. 2 is a cross-sectional representation of a treated microporous film shown in FIG. 1 taken at A—A'.
Figure 9:
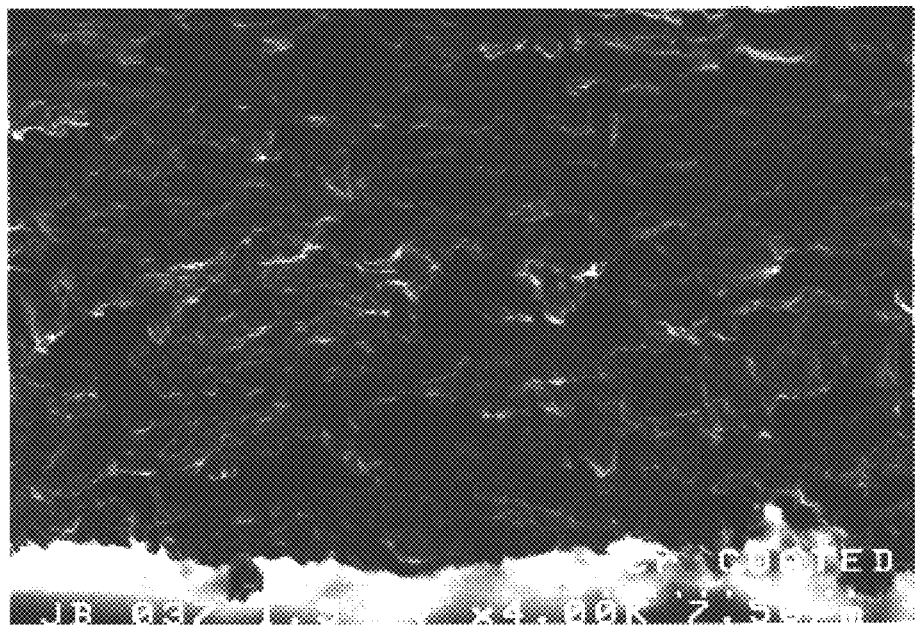
FIG. 9 is a photomicrograph of an untreated region of a microporous breathable film.
Figure 10:
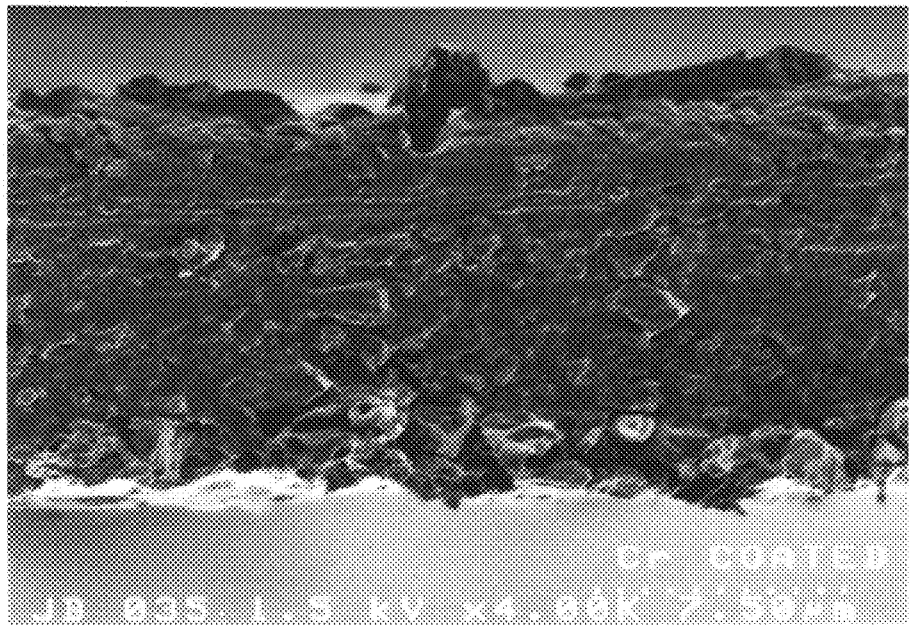
FIG. 10 is a photomicrograph of a treated region of the same microporous film shown in FIG. 9.

The zoned treatment of the microporous film acts to reduce the number and/or size of the pores in the treated regions thereby reducing the WVTR or breathability in those same regions. In reference to FIGS. 1 and 2, the zone treated microporous film can have a first substantially uncompressed region 24 which has a higher level of breathability than the second compressed region 26 of the film. The compressed or second region 26 will substantially correspond to those areas of the film to which heat and/or pressure is applied via the raised regions 22 of the patterned nip roll 18. In addition, the treated regions will, despite having a lower WVTR, typically have a thickness which is thinner than the substantially uncompressed regions. Although the relative thickness will vary, the compressed regions desirably have a thickness which is less than about 95% of the thickness of the untreated region and in other embodiments can be less than about 90% or even less than about 80% of the thickness of the untreated regions. In this regard it is believed that the decrease in film thickness provides a corresponding decrease in porosity. However, as a result of heat treatment, some retraction may occur changing the film basis weight. Further, as a result of retraction, the treated regions of the film may have a thickness substantially equal to that of the treated regions. FIGS. 9 and 10, respectively, are photomicrographs of a cross-section of a substantially uncompressed region of a stretched, filled microporous film and a compressed region of the same film. In addition, with microporous stretched filled-films of about 35 g/m² or less, upon application of sufficient heat and pressure, the compressed regions can become translucent and/or exhibit decreased opacity relative to the substantially uncompressed regions.

In a further aspect of the invention, thermoplastic polymers can be utilized in the microporous films whereby controlled regional breathability can be achieved utilizing little or no mechanical compacting pressure. This may have the advantage of providing a film with improved hydrohead levels and/or a more durable or stronger film. In this regard, zoned or regional treatment of the microporous thermoplastic polymer film with sufficient energy, such as heat, causes the thermoplastic polymer to soften and/or create a sufficiently high melt fraction which results in a decrease in the porosity of the microporous film and a corresponding decrease in the breathability of the film. Various forms of energy may be used to induce polymer softening and/or a significant melt fraction and include, but are not limited to, thermal, ultrasonic, infra-red, microwave and other forms of electromagnetic energy. Suitable polymers include thermoplastic polymers such as those described herein above and, in particular, polyolefin polymers such as polyethylene, polypropylene and copolymers and blends thereof.

A breathable barrier film having varied regional breathability can be made from a monolayer microporous film comprising a thermoplastic polymer. Alternatively, a breathable barrier film having varied regional breathability can be made from multilayer films wherein at least one of the layers comprises a microporous thermoplastic polymer layer. Utilization of a multilayer film may provide several advantages relative to monolayer films. Certain zoned treatments of the thermoplastic polymer film, such as with heat, can cause the treated regions to experience localized or regional shrinkage since the film is not uniformly treated across its entire surface. The regional shrinkage may thus cause stress within the film as well as buckling or sagging of the film. In this regard utilizing a multilayer film in which one of the layers is substantially unaffected by the regional treatment can provide additional support to the overall film and thereby reduce and/or eliminate shrinkage of the zone treated regions and any deleterious effects associated with the same. In a particular embodiment, the multilayer film comprises at least one layer of a microporous film of a heat sensitive polymer and a second layer or base film layer which is substantially unaffected by the treatment necessary to reduce the porosity and WVTR of the first or heat sensitive layer. The base film layer can comprise either a monolithic film layer (i.e. non-porous) or a microporous film comprising a heat stable thermoplastic polymer. As used herein, the term "heat stable" is with respect to or with relation to the corresponding "heat sensitive" layer. Thus, a given microporous thermoplastic polymer film can be "heat sensitive" with relation to certain films and "heat stable" with respect to others. Where the base or heat stable film comprises a microporous thermoplastic polymer film, a heat sensitive microporous film is one in which the polymer experiences onset of significant molten fraction sufficient to cause decreased porosity and a drop in WVTR at least 10° C. below the softening point of the polymer comprising the base film, and even more desirably at least 20° C. below the softening point of the polymer comprising the base film.

Exemplary monolithic films include, but are not limited to, polyether-amid polymers, polyvinyl alcohol polymers, polyether-ester polymers, nylon copolymers and polyurethane polymer films since, although non-porous, the functionality of the polymer provides excellent diffusion of water vapor through the film and thus good breathability. Examples of such commercially available polymers include, by way of example, ESTANE 58690 polyurethene polymer available from B. F. Goodrich Company. HYDROFIL nylon resin available from Allied Signal, Inc., of Morristown, N.J., PEBAX polyether-polyamide block copolymers available from Elf Atochem of North America, Inc., of Philadelphia, Pa. Alternatively, preferred microporous base layer comprises a linear low density polyethylene (LLDPE) polymer microporous films. LLDPE microporous films are relatively robust and able to retain a highly breathable, microporous structure when subjected to heat. Linear low density polyethylene films typically comprise copolymers of ethylene and an alpha-olefin, having a density ranging from about 0.91 g/cm³ to about 0.92 g/cm³. Of course one skilled in the art will recognize that at sufficiently high temperatures LLDPE will soften or melt and thereby experience decreased porosity and breathability. However, its ability to substantially retain its micropore structure and WVTR at temperatures approaching up to about 210° F. (98° C.) makes LLDPE heat stable relative to many other good film forming polymers. For example, polyethylene plastomers (i.e. polyethylene having a density less than about 0.89 g/cm³) are heat sensitive polymers relative to LLDPE polymer films and tend to be less robust in terms of retaining a porous structure when exposed to heat or other energy. Thus, as a particular example, when using a LLDPE microporous film as a base layer, microporous polymer films such as polyethylene plastomers which experience a reduction in porosity and WVTR at temperatures of about 140° F. would comprise "heat sensitive" polymers.

Elastic polyolefins and/or polyolefin plastomers are preferred heat sensitive polymers and can be made by "metallocene", "constrained geometry" or "single-site" catalysts such as those described in U.S. Pat. No. 5,472,775 to Obijeski et al.; 5,451,450 to Erderly et al.; 5,204,429 to Kaminsky et al.; 5,539,124 to Etherton et al.; and 5,554,775 to Krishnamurti et al.; the entire contents of each of which are incorporated herein by reference. Regarding such elastomeric polymers, U.S. Pat. No. 5,204,429 to Kaminsky et al. describes a process which may produce elastic copolymers from cycloolefins and linear olefins using a catalyst which is a stereorigid chiral metallocene transition metal compound and an aluminoxane. The polymerization is carried out in an inert solvent such as an aliphatic or cycloaliphatic hydrocarbon such as toluene. U.S. Pat. Nos. 5,278,272 and 5,272,236, both to Lai et al., assigned to Dow Chemical and entitled "Elastic Substantially Linear Olefin Polymers" describe polymers having particular elastic properties, the entire contents of each of which are incorporated herein by reference. By way of example, suitable low density ethylene elastomers are commercially available from Dow Chemical Company of Midland, Mich. under the trade name AFFINITY, and from Exxon Chemical Co. of Houston, Tex., under the trade name EXACT.

Other exemplary commercially available heat sensitive polymers include, but are not limited to, olefin multi-step reactor products wherein an amorphous ethylene propylene random copolymer is molecurlarly dispersed in a predominately semi-crystalline high propylene monomer/low ethylene monomer continuous matrix. Examples of such polymers are described in U.S. Pat. No. 5,300,365 to Ogale; U.S. Pat. No. 5,212,246 to Ogale and U.S. Pat. No. 5,331,047 to Giacobbe. Such polymers are commercially available from Himont, Inc., under the tradename CATALLOY such as, for example, CATTALLOY KS350, KS357 and KS359.

Additionally, ethylene/propylene copolymers such as the REXTAC family of amorphous polyalphaolefins from Huntsman Corp. and VESTOPLAST polymers from Creanova AKG are additional heat sensitive polymers suitable for use with the present invention. In this regard it is important to note that although such polymers may have a higher melting point than LLDPE, microporous films of certain polymers, such as ethylene/propylene copolymers, can experience a loss of porosity or decrease in WVTR at temperatures which do not substantially affect the pore structure of a LLDPE film. This is believed to result from onset of a significant molten fraction within the microporous polymer films, due to the amorphous polymer content, which allows the relief of stresses within the film and collapsing or shrinkage of the pores.

Additional exemplary heat sensitive polymers, utilized either alone or in combination with other polymers, include but are not limited to, ethylene vinyl acetate (EVA), ethylene ethyl acrylate (EEA), ethylene acrylic acid (EAA), ethylene methyl acrylate (EMA), ethylene normal butyl acrylate (EnBA) and the like. Further, blends of polyolefins such as polyethylene and/or polypropylene with the aforesaid polymers are believed particularly well suited to practicing the present invention.

As an example, a breathable microporous film suitable for use with the present invention can comprise a multilayer film having a composition, such as those described in U.S. patent application Ser. No. 08/882,712 (pending) filed Jun. 25, 1997 to McCormack et al.; and U.S. Pat. No. 6,045,900 to Haffner et al. As a particular example, the core layer can comprise a LLDPE filled microporous film and one or more outer or skin layers can comprise a microporous film of a heat sensitive polymer such as, for example, a polyethylene plastomer filled film. In a further aspect, the outer or skin layers may comprise ethylene/propylene copolymers or a polyethylene elastomer/EVA blend, polyethylene elastomer/EMA blend. Desirably, the outer layer comprises the heat sensitive polymer layer and has a thickness of at least about 10% of the total multilayer film thickness and still more desirably has a thickness between about 15% and about 45% of the total multilayer film thickness.

Figure 11:
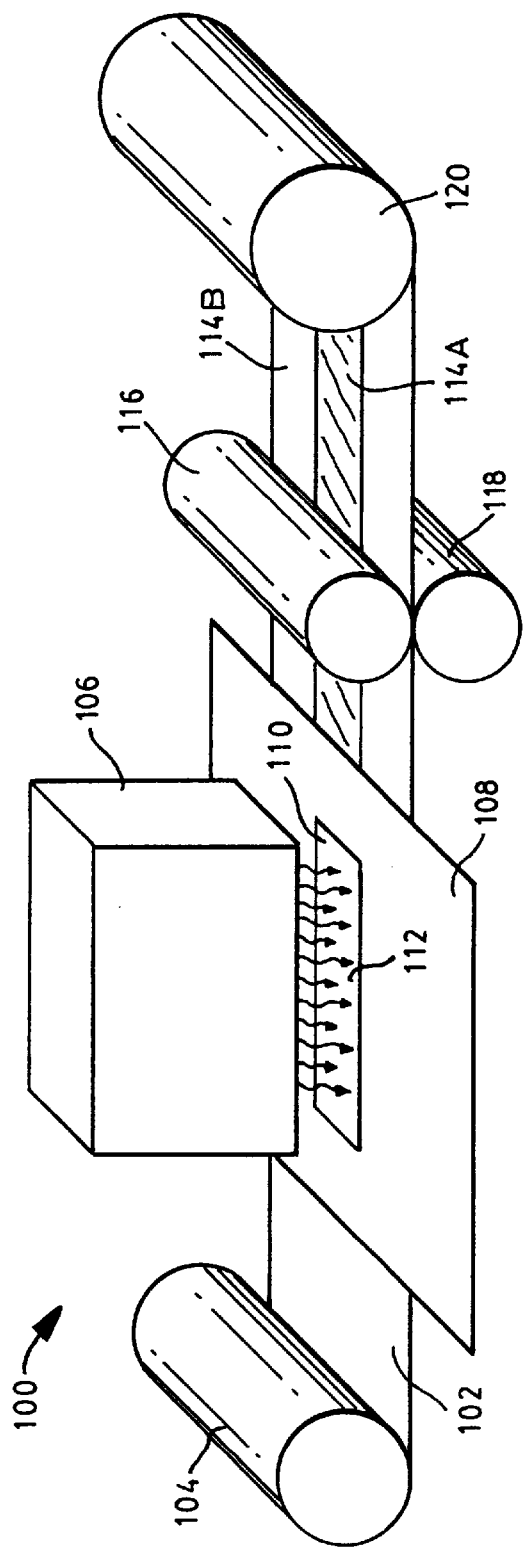
FIG. 11 is a schematic representation of an exemplary focused hot air assembly suitable for practicing the present invention and a zone treated film made therefrom.
Figure 12:
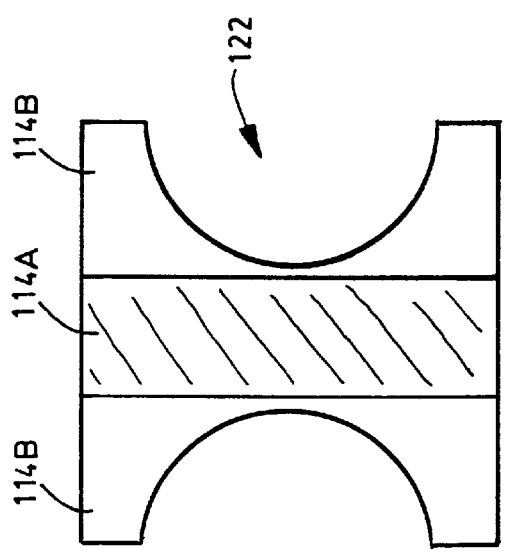
FIG. 12 is a plan view of an outer cover for a diaper or incontinence garment converted from the zone treated regionally breathable film of FIG. 11.

Breathable microporous films comprising thermoplastic polymers, such as those films indicated above, can be treated with heat and/or other energy to regionally reduce porosity of the film and create a film having controlled regional breathability. Such films can be treated by use of a stream of focused heated air which is directed such that it substantially impacts only the desired regions of the film. Thus, the treated film can have relative regions of high and low breathability with the regions directly impacted by the heated air having reduced water vapor transmission rates. Of course, due to the fluid nature of air, a film treated by such means will likely exhibit a breathability gradient as opposed to the more distinctly delineated regions achievable by stepped nip rolls and/or use of other more precisely controlled energy sources. The heated air can be focused by use of strategically placed shielding and/or masks, the particular positioning of which will vary with the pattern of reduced breathability regions desired upon the film. As an example and in reference to FIG. 11, breathable microporous film 102 can be unwound from a supply roll 104 and fed under blower 106 and shielding 108 such as a patterned or slotted plate. Hot air 110 passes through opening 112 shielding 108 thereby directly impacting only the selected portion of film 102. The heat from hot air 110 cause the pores within the central portion of film 102 to substantially deform and/or collapse which results in film 114 having first region 114A of low breathability along the central region of the film and second region 114B along the edges and/or outer portions of the film. The shim and/or mask can be cooled as necessary by means well known in the art. Optionally, in order to further increase the degree to which porosity is decreased a pair of smooth nip rolls 116, 118 can be used to apply a light compacting pressure to the film immediately after regionally heating film 102. Desirably, the nip rolls impart only a light compacting pressure and impart a force of less than about 75 pli and still more desirably between 25 and 50 pli. The treated film 114 can be wound on a winder roll 120 and alternatively can be converted in-line as desired. As a particular example and in reference to FIG. 12, treated film 114 can be readily converted into a baffle 122 for a personal care article, such as a diaper, wherein the region of reduced breathability 114A is positioned along the central portion of the baffle 122 and whereby the region of reduced breathability 114A is disposed along the crotch of the corresponding absorbent personal care article.

Figure 13:
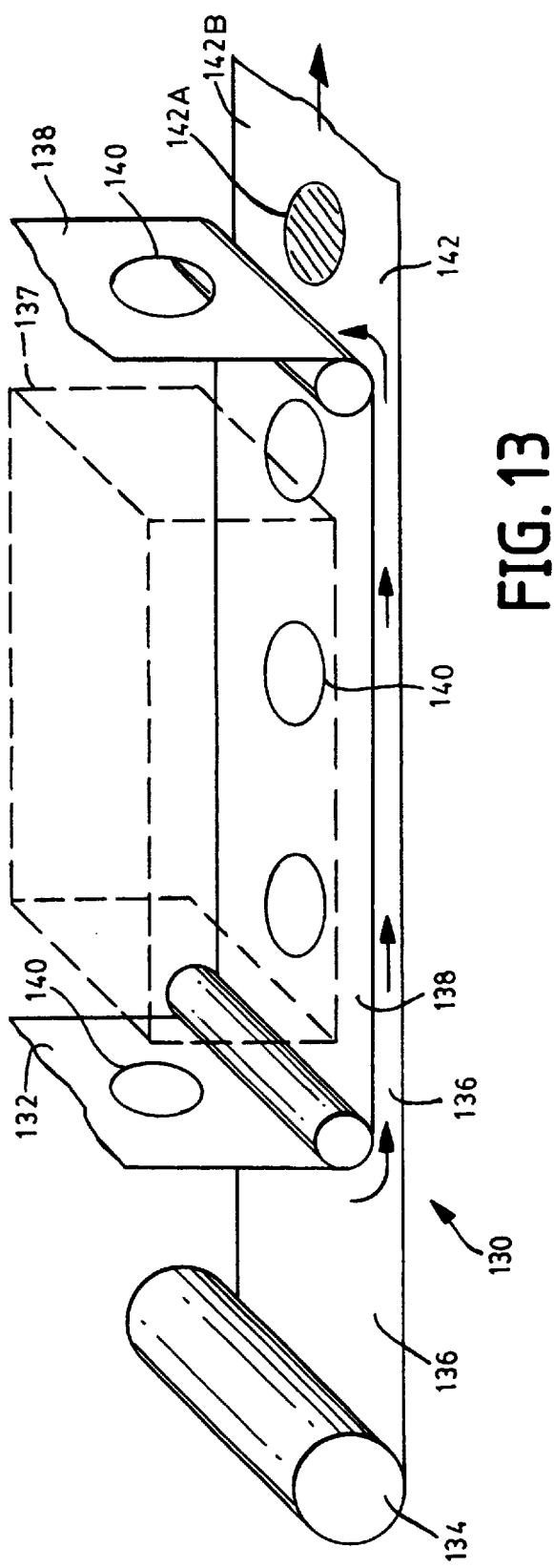
FIG. 13 is a schematic representation of an exemplary focused hot air assembly suitable for practicing the present invention and a zone treated film made therefrom.
Figure 14:
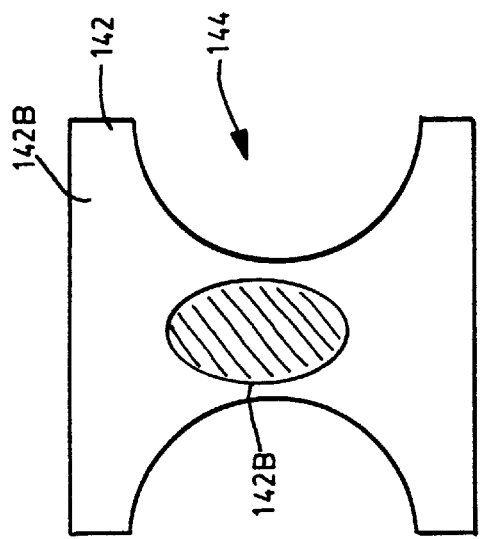
FIG. 14 is a plan view of an outer cover for a diaper or incontinence garment converted from the zone treated regionally breathable film of FIG. 13.

In a further example and in reference to FIG. 13, breathable microporous film 136 can be fed under a moving or rotating shield or mask 138. Microporous film 136 can be unwound from a supply roll 134 as shown. However, with this and the other schematic diagrams and/or processes described herein, it will be appreciated that microporous film 136 could alternatively be made in-line. Microporous film 136 is fed under mask 138 having openings 140 disposed therein which are of a desired shape and frequency. Openings 140 are positioned above microporous film 136 in order to selectively reduce breathability of microporous film 136 in desired regions of the film. The shape and location of the regions of reduced breathability 142A will substantially correspond to the shape and positioning of openings 140 within shielding 138. Thus, treated microporous film 142 can comprise selected first regions 142A of a desired shape and location having reduced breathability and second regions 142B having higher breathability. The reduced breathability region 142B can have any one of various shapes including, but not limited to, an oval or elliptical shape. In one embodiment, shielding 138 can be rotated or moved in the same direction and speed as microporous film 136 in order to achieve the desired duration of treatment. Energy source 137 (shown in phantom), such as hot air blower or a infrared light source, can be positioned such that shielding 138 is disposed between energy source 137 and microporous film 136 wherein only selected regions, directly exposed to the energy source via openings 140, are impacted by the hot air or other energy resulting in low WVTR regions relative to the unexposed regions. Thus, treated microporous film 142 can comprise selected first regions 142A of a desired shape and location having reduced breathability and second regions 142B having higher breathability. The treated microporous film can be wound and/or converted as discussed herein. As an example and in reference to FIG. 14, treated film 142 can be converted into an outer cover or a baffle 144 for a personal care article, such as a diaper, wherein a reduced breathability region 142B is positioned about the central portion of baffle 144 and higher breathability regions 144 are located at the outer regions and/or ears of the baffle. In one aspect of the invention, the reduced breathability region 142B can be located about the crotch of a diaper or incontinence garment. Further, reduced breathability region 142B can be positioned more towards the front or back of a incontinence garment as desired to create a gender specific absorbent personal care articles.

Alternate energy sources, other than thermal energy (i.e. heat), can likewise be used to treat breathable microporous films so as to selectively or regionally reduce breathability. As examples thereof, alternate energy sources include, but are not limited to, ultrasonic energy and radiation suitable for heating such substrates such as, for example, infra-red light or microwave (tuned to one or more components of the polymers and/or filler). These alternate energy sources could be substituted for the hot air blowers depicted in FIGS. 11 and 13 to selectively treat a microporous film as desired. As an example, and in reference to FIG. 11, a high intensity infra-red light source can be substituted for the hot air blower 106. Use of high intensity infra-red light will likely provide a treated film having more distinctly delineated regions of varied breathability as compared to films treated with hot air due to the ability to more precisely focus infra-red radiation. The configuration and/or composition of shielding selected will vary in accord with the particular form of energy emitted by the energy source. Additionally, utilization of heat removal devices and/or cooling means can be used in conjunction with the shielding as desired. Exemplary devices include, but are not limited to, chilled rolls and cooled air.

It will be appreciated by those skilled in the art that variations in the process design and/or equipment may be made without departing from the scope of the present invention. As an example, for each of the examples described herein, it is possible to make the microporous film and/or any additional components in-line thereby having a single continuous process without the need to roll or store materials between various processing, treatment and/or converting operations.

In a further aspect of the invention, the microporous film having zoned breathability can be joined with one or more additional layers of breathable material. In one aspect, the microporous film can be attached to a pliable support layer capable of being laminated to the film such as, for example, a pliable fibrous material, film and/or foam. Exemplary fibrous layers include, but are not limited to, nonwoven webs, multilayer nonwoven laminates, scrims, woven fabrics, slit films and/or other like materials. In a particular embodiment, the support fabric can comprise one or more layers of spunbonded and/or meltblown fiber webs including, but not limited to, monocomponent spunbond fiber webs, multicomponent spunbond fiber webs, multiconstituent fiber webs, split fiber webs, multilayer nonwoven laminates and the like. Generally, the composition of the fibrous layer may be selected to achieve the desired properties, e.g. hand, aesthetics, tensile strength, cost, abrasion resistance, hook engagement, etc. Further, the fibrous layer can also be treated such as, for example, by embossing, hydroentangling, mechanically softening, printing or treated in another manner in order to achieve additional desired characteristics. In one embodiment the outer layer may comprise about a 10 g/m$^2$ to about 68 g/m$^2$ web of spunbonded polyolefin fibers and even more desirably a 10 g/m$^2$ to about 34 g/m$^2$ web of such fibers. The fibrous layer can be attached or laminated to the microporous film by adhesive bonding, thermal bonding, ultrasonic bonding or other means known in the art. In one aspect of the invention the microporous film and fibrous layer are bonded with an adhesive sprayed via a standard meltblown die to either the nonwoven fabric and/or film. In a further aspect of the invention, a thermoplastic polymer nonwoven web and microporous film can be laminated via thermal point-bonding.

In still a further aspect of the invention, the microporous film can be attached to additional materials, such as those described above, prior to the treatment to the microporous film to impart zoned breathability. When treated with significant compacting pressure additional materials bonded to the microporous film may experience an unwanted decrease in bulk and/or hand. In this regard, breathable microporous films are often bonded with cloth-like materials and disposed within an article such that the cloth-like material faces outward and is thus the material touched when handling the article. Compaction of such materials may degrade the softness of the outer layer and/or otherwise detract from the aesthetics of the same. Accordingly, when treating microporous film laminates where bulk and/or aesthetics are of concern it may be advantageous to treat such laminates using one of the above methods requiring little or no compacting pressure. Additionally, the ability to treat a microporous film laminate without significantly detracting from the bulk and/or aesthetics of the article may provide additional processing advantages. In a high speed manufacturing process there may be difficulties experienced in registering the reduced breathability areas in a converting line, thereby making it difficult to ensue that the areas of reduced breathability are properly positioned in the converted article. In this regard, utilization of microporous film laminates capable of treatment to create zoned breathable regions has the advantage of allowing treatment of the microporous film after the same has been converted without significantly compromising the desired characteristics of the nonwoven fabric attached thereto.

Figure 15:
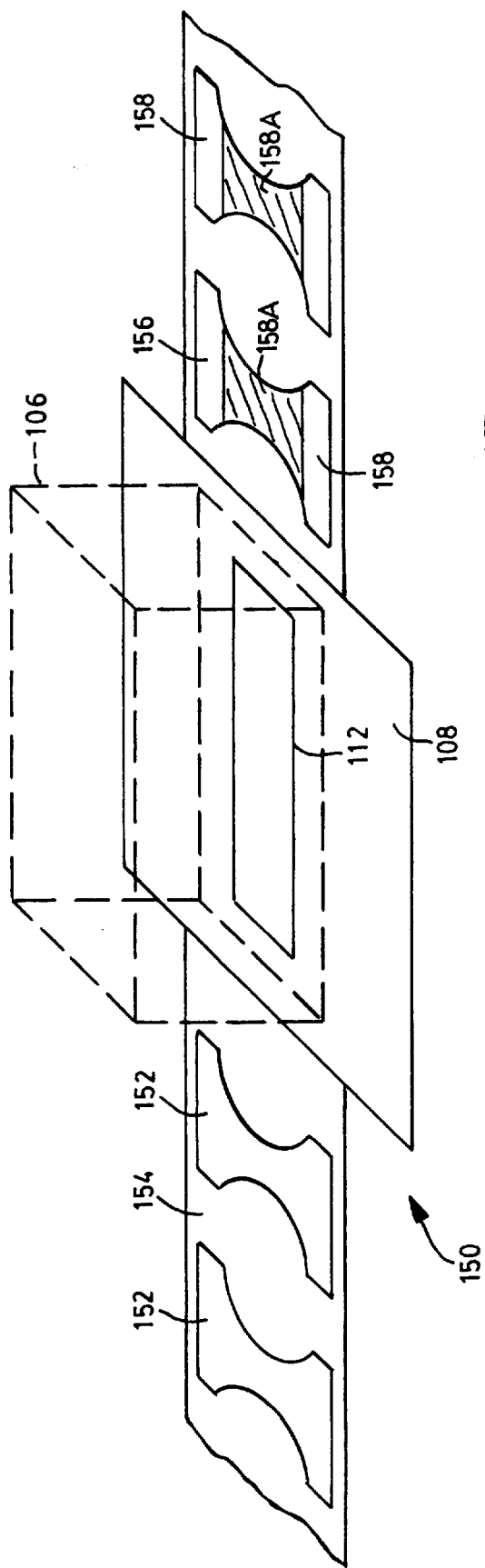
FIG. 15 is a schematic representation of an exemplary focused hot air assembly suitable for practicing the present invention and converted zone treated film laminates made therefrom.
Figure 16:
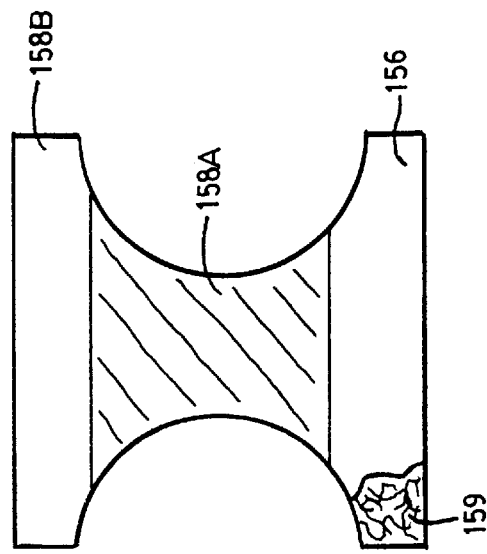
FIG. 16 is a plan view of a film/nonwoven laminate outer cover for a diaper or incontinence garment treated in accord with the process of FIG. 15.

As a particular example and in reference to FIGS. 15 and 16, film/nonwoven laminate 152, comprising a breathable microporous film 153 fixedly attached to a nonwoven web 159, can be converted as desired such as in the shape of a baffle or outer cover for use in a diaper or incontinence garment. The untreated film/nonwoven laminate 152 can have a nonwoven fabric 159 permanently bonded to breathable microporous film 153 by means of adhesive, thermal point bonding, ultrasonic bonding or other like means. With the film side facing the energy source, the converted film/nonwoven laminate 152 can travel, via belt 154, under a hot air blower 106 (shown in phantom) and shielding 108 whereby only the desired regions of film/nonwoven laminate 152, namely those regions exposed to the hot air through slot 112, have their breathability reduced. The treated film/nonwoven laminates 156 thus have first region 158A of reduced breathability and second regions 158B of comparatively higher breathability. In a particular embodiment, when fitted within a diaper, the film/nonwoven laminate 156 can have the treated region of reduced breathability 158A centered about the crotch and regions of higher breathability 158B at the outer regions of the article. Moreover, due to the nature of the film treatment, the bulk and/or hand of nonwoven fabric 159 remains substantially unchanged. In a further aspect, the zone treated film can optionally be fed through a pair of rollers immediately after the zoned treatment to regionally reduce breathability of the film. Such a light compacting force of the rollers causes additional increase in density and decrease in porosity in the treated regions. The rollers can be flat and need not be heated. Light compacting pressures can be utilized such as, for example, those between 25 and 50 pli. The treated regions have a significant molten fraction immediately following such treatment and thus are readily deformed or compacted upon experiencing a light compacting pressure. However, the untreated regions on the film are not as susceptible to such compaction since they lack a significant molten fraction and therefore do not experience significant loss of porosity and/or WVTR. Additionally, resilient materials having a softening point at least 10° C., and desirably over 20° C., greater than that of the polymeric component of the zone treated microporous film also resist significant compaction or densification. Thus, the materials attached to the zone treated film can maintain a substantially uniform bulk and/or appearance as well as good hand such as is desired for backings of personal care articles and diapers in particular.

The microporous films of the present invention having controlled regional breathability can be used with a wide variety of products or as components of products such as, for example, in personal care articles, infection control products, protective covers, garments and the like. As discussed, a microporous film similar to those discussed above can be readily converted and incorporated within a breathable barrier of a diaper or incontinence garment and further could be readily converted for use in one or more additional personal care articles. As a further example, the zoned breathability microporous films may be used in surgical gowns. It is believed that the regions of reduced breathability, particularly areas where breathability has been significantly or almost completely reduced, may provide improved barrier properties. For example, areas of reduced breathability are believed to provide improved barrier properties to blood borne pathogens. Thus, surgical gowns can be fabricated employing the treated or low breathability regions within high risk areas and higher WVTR regions within lower risk areas. High risk areas can include those areas which are more prone to insult such as, for example, the forearms of the gown. The microporous film can also be advantageously utilized in numerous other applications employing breathable barrier fabrics.

Tests

Hydrohead: A measure of the liquid barrier properties of a fabric is the hydrohead test. The hydrohead test determines the height of water or amount of water pressure (in millibars) that the fabric will support before liquid passes therethrough. A fabric with a higher hydrohead reading indicates it has a better barrier to liquid penetration than a fabric with a lower hydrohead. The hydrohead can be performed according to Federal Test Standard 191A, Method 5514. The hydrohead data cited herein was obtained using a test similar to the aforesaid Federal Test Standard except modified as noted below. The hydrohead was determined using a hydrostatic head tester available from Marl Enterprises, Inc. of Concord, N.C. The specimen is subjected to a standardized water pressure, increased at a constant rate until the first sign of leakage appears on the surface of the fabric in three separate areas. (Leakage at the edge, adjacent to clamps is ignored.) Unsupported materials, such as a thin film, are supported to prevent premature rupture of the specimen.

WVTR: The water vapor transmission rate (WVTR) for the sample materials was calculated in accordance with ASTM Standard E96-80. Circular samples measuring three inches in diameter were cut from each of the test materials and a control which was a piece of CELGARD 2500 film from Hoechst Celanese Corporation of Sommerville, N.J. CELGARD 2500 film is a microporous polypropylene film. Three samples were prepared for each material. The test cups were number 68-1 Vapometer cups distributed by Thwing-Albert Instrument Company of Philadelphia, Pa. One hundred milliliters of water were poured into each vapometer cup and individual samples of the test materials and control material were placed across the open tops of the individual pans. The vapometer cups were mechanically sealed along the edges of the cup, leaving the associated test material or control material exposed to the ambient atmosphere over a 6.8 centimeter diameter circle having an exposed area of approximately 33.17 square centimeters. The cups were placed in a convection type oven at 100° F. (37.7° C.) for 24 hours. The oven was a constant temperature oven with external air circulating through it to prevent water vapor accumulation inside. After 24 hours, the pans were removed from the oven and weighed again. The preliminary test water vapor transmission rate values were calculated with Equation (I) below:

$$\text{Test WVTR}=(\text{grams weight loss over 24 hours})\times 315.5 \text{ g/m}^2/24 \text{ hours} \quad (I)$$

The relative humidity within the oven was not specifically controlled. Under the predetermined set conditions of 100° F. (37.7° C.) and ambient relative humidity, the WVTR for the CELGARD™ 2500 control has been defined to be 5000 grams per square meter for 24 hours. Accordingly, the control sample was run with each test and the preliminary test values were corrected to set conditions using Equation (II) below:

$$\text{Standardized WVTR}=(\text{Test WVTR/control WVTR})\times(5000 \text{ g/m}^2/24 \text{ hours}) \quad (II)$$

Strip Tensile: The strip tensile test measures the peak and breaking loads and peak and break percent elongations of a fabric. This test measures the load (strength) in grams and elongation in percent. In the strip tensile test, two damps, each having two jaws with each jaw having a facing in contact with the sample, hold the material in the same plane, usually vertically, separated by 3 inches and move apart at a specified rate of extension. Values for strip tensile strength and strip elongation are obtained using a sample size of 3 inches by 6 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Philadelphia, Pa. 19154 may be used for this test. Results are reported as an average for ree specimens and may be performed with the specimen in the cross direction (CD) or the machine direction (MD).

EXAMPLE I

A cast extruded film was made, comprising linear low density polyethylene (0.918 g/cm$^3$ from Dow under the designation DOWLEX NG 3310) and 48% by weight calcium carbonate (available from English China Clay of America, Inc. under the designation SUPERCOAT) coated with stearic acid. The filled film was then heated and stretched 500% of original length using a machine direction orientor unit to create a microporous film having a basis weight of approximately 14 g/m$^2$. The resulting breathable microporous film had a WVTR of 2358 g/m$^2$/24 hours, a MD strip tensile of 6987 g and a CD strip tensile of 425 g. The breathable microporous film was wound on a supply roll and subsequently unwound and fed through a pair of nip rolls at a speed of 50 feet/minute. Both rolls were steel rolls and the upper roll was patterned having a configuration similar to that shown in FIGS. 1 and 3, having a raised region with a width of 8 inches extending about the center of the roll. The lower roll was a flat anvil roll. The nip pressure and temperature of rolls were varied in order to obtain varied levels of regional breathability, the results of which are shown on Table I.

EXAMPLE II

The microporous stretched filled-film described in Example I was laminated to a nonwoven web. The microporous film was sprayed with 3 g/m² of adhesive (amorphous polyalphaolefin adhesive available from Huntsman Polymer Corporation under the trade name RT 2730) and immediately thereafter a 17 g/m² polypropylene spunbond fiber nonwoven web was juxtaposed with and pressed against the microporous film by a pair of unpatterned nip rolls. The laminate was subsequently zone treated at a rate of 50 feet/minute using the nip rolls as described in Example 1. The process conditions and resulting physical attributes of the laminates are described in Table II. The film laminate, or to zone treatment, had a peel strength of 860 g, a hydrohead of 162 mbar and a WVTR 2457 g/m²/24 hours.

TABLE I

| Trial | Anvil #1 Temp. °F. (Actual) | Anvil #2 Temp. °F. (Actual) | Nip Pressure PLI PSIG | WVTR g/m²/24 hours | Strip Tensile CD | MD |
|---|---|---|---|---|---|---|
| 1 | 75 | 75 | 15 | 88 | 2210 | 6399 | 459 |
| 2 | 75 | 75 | 30 | 145 | 1660 | 6031 | 441 |
| 3 | 75 | 75 | 45 | 215 | 1399 | 6208 | 442 |
| 4 | 75 | 75 | 60 | 297 | 1426 | 6054 | 436 |
| 5 | 105 | 105 | 15 | 88 | 1914 | 6453 | 465 |
| 6 | 105 | 105 | 30 | 145 | 1548 | 5991 | 452 |
| 7 | 105 | 105 | 45 | 215 | 1243 | 6347 | 450 |
| 8 | 105 | 105 | 60 | 297 | 1033 | 5331 | 449 |
| 9 | 123 | 123 | 15 | 88 | 1657 | 6638 | 461 |
| 10 | 123 | 123 | 30 | 145 | 1385 | 6329 | 467 |
| 11 | 123 | 123 | 45 | 215 | 1148 | 5961 | 458 |
| 12 | 123 | 123 | 60 | 297 | 1012 | 5172 | 461 |
| 13 | 150 | 150 | 15 | 88 | 1471 | 6613 | 470 |
| 14 | 150 | 150 | 30 | 145 | 1192 | 6232 | 477 |
| 15 | 150 | 150 | 45 | 215 | 1067 | 6336 | 483 |
| 16 | 150 | 150 | 60 | 297 | 1542 | 6523 | 441 |
| 17 | 170 | 170 | 15 | 88 | 1878 | 6938 | 445 |
| 18 | 170 | 170 | 30 | 145 | 1234 | 6626 | 461 |
| 19 | 170 | 170 | 45 | 215 | 1174 | 6794 | 471 |
| 20 | 170 | 170 | 60 | 297 | 851 | 6481 | 474 |
| 21 | 195 | 195 | 15 | 88 | 970 | 6917 | 496 |
| 22 | 195 | 195 | 30 | 145 | 583 | 6800 | 503 |
| 23 | 195 | 195 | 45 | 215 | 538 | 6568 | 601 |
| 24 | 195 | 195 | 60 | 297 | 219 | 6683 | 604 |
| 25 | 220 | 220 | 15 | 88 | 185 | 6947 | 610 |
| 26 | 220 | 220 | 30 | 145 | 95 | 7308 | 737 |
| 27 | 220 | 220 | 45 | 215 | 59 | 6828 | 735 |
| 28 | 220 | 220 | 60 | 297 | 62 | 6893 | 740 |

TABLE II

| Trial | Anvil #1 Temp. °F. (Actual) | Anvil #2 Temp. °F. (Actual) | Nip Pressure PLI PSIG | WVTR g/m²/ 24 hours | Hydrohead Mbar |
|---|---|---|---|---|---|
| 1 | 75 | 75 | 30 | 145 | 2138 | 144 |
| 2 | 75 | 75 | 60 | 297 | 1970 | 116 |
| 3 | 130 | 130 | 30 | 145 | 1979 | 111 |
| 4 | 130 | 130 | 60 | 297 | 1521 | 111 |
| 5 | 220 | 220 | 30 | 145 | 430 | 82 |
| 6 | 220 | 220 | 60 | 297 | 347 | 52 |

The following examples are given to illustrate representative additional templated specific embodiments of the invention.

EXAMPLE III

A two-layer film is coextruded using conventional cast film extrusion technology such that the first layer is substantially continuously joined in a face-to-face relation with a second layer. The first layer or base layer is about 80% of the total film thickness and comprises about 55% by weight calcium carbonate particles (available from English China Clay of America, Inc. under the designation SUPERCOAT) coated with stearic acid, about 22.5% polyethylene plastomer (AFFINITY EG 8200 polymer, 0.87 g/cm³, 5 MI available from Dow Chemical Co.), about 22.5% linear low density polyethylene (AFFINITY PL 1845 polymer, 0.91 g/cm³, 3.5 MI available from Dow Chemical Co.). The second layer is about 20% of the overall thickness of the multilayer film and comprises about 62% by weight calcium carbonate filler (available from English China Clay of America, Inc. under the designation SUPERCOAT) coated with stearic acid, about 19% polyethylene plastomer (AFFINITY EG 8200 polymer as described above), and about 19% amorphous polyalphaolefin (REXTAC 2503-3A, an amorphous, low viscosity polymer, comprising primarily of ethylene and butene, which is available from Huntsman Corp. of Houston, Tex.). Extruded basis weight of the two-layer film is 100 g/m². The two-layer film is stretched in a machine-direction 24 orientor (MDO) about three times its original length thereby rendering the film microporous. After allowing the stretched film to retract slightly over a heated roll, the microporous film will have a basis weight of about 34 g/m². The microporous film is pattern bonded to an extensible polypropylene spunbond fabric to form a cohesive laminate. The laminate is zone treated using a heated steel roll with a five inch wide raised surface pressing against an unheated smooth, rubber covered pressure roll. The laminate is fed into the roll assembly with the film side facing the rubber covered roll. Temperature of the heated roll is approximately 175° F. and the nip pressure (in the region corresponding with the raised surface) is about 100 pounds per linear inch (pli). The resulting film laminate will have a hydrohead in excess of 50 mbars and regions having (relative to one another) high and low WVTR levels. More particularly, the region fed under the raised portion of the heated steel roll will have a WVTR lower than adjacent regions.

EXAMPLE IV

A two-layer film is coextruded using conventional cast film extrusion technology such that the first layer is substantially continuously joined in a face-to-face relation with a second layer. The first layer or base layer is about 80% of the total film thickness and comprises about 55% by weight calcium carbonate particles (available from English China Clay of America, Inc. under the designation SUPERCOAT) coated with stearic acid, about 22.5% linear low density polyethylene (DOWLEX 2035 polymer, 0.919 g/cm³, 6 MI available from Dow Chemical Co.), and about 22.5% linear low density polyethylene (AFFINITY PT 1409 polymer, 0.911 g/cm³, 6 MI available from Dow Chemical Co.). The second layer is about 20% of the overall thickness of the multilayer film and comprises about 62% by weight calcium carbonate filler (available from English China Clay America, Inc. under the designation SUPERCOAT) coated with stearic acid, about 19% polyethylene plastomer (AFFINITY EG 8200 polymer as described above), and about 19% amorphous polyalphaolefin (REXTAC 2503-3A, an amorphous, low viscosity polymer, comprising primarily of ethylene and butene, available from Huntsman Corp. of Houston, Tex.). Extruded basis weight of the two-layer film is 100 g/m². The two-layer film is stretched in a machine-direction orientor (MDO) about four times its original length rendering the film microporous. After allowing the stretched film to retract slightly over a heated roll, the microporous film will have a basis weight of about 34 g/m². The microporous film is pattern bonded to an extensible spunbond fabric to form a cohesive laminate. The laminate is zone treated using a heated steel roll with a five inch wide raised surface pressing against an unheated smooth, rubber covered pressure roll. The film side of the laminate is fed into the roll assembly facing the rubber covered roll. Temperature of the heated roll is approximately 175° F. and the nip pressure (in the region corresponding with the raised surface) is about 100 pounds per linear inch (pli). The resulting film laminate will have a hydrohead in excess of 50 mbars and regions of varied breathability levels. More particularly, the region fed under the raised portion of the heated steel roll will have a WVTR lower than adjacent regions.

While various patents and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the appended claims cover all such modifications, alterations and other changes.

We claim:

1. A film comprising:
   a first microporous region having a thickness less than about 50 $\mu$ and a WVTR of at least 800 g/m$^2$/24 hours;
   a second region having a greater density than that of the first region wherein the WVTR of the second region is at least 15% less than the WVTR of the first region and said second region is substantially uniform and has a thickness substantially equal to or less than that of said first region and further wherein said second region has dimensions not less than 3 cm by 5 cm; and
   said film having a hydrohead of at least about 50 mbar.

2. The breathable film of claim 1 wherein said thermoplastic polymer comprises a polyolefin polymer and wherein the second region has minimum dimension of 5 cm by 10 cm.

3. The breathable film of claim 2 wherein said second region extends at least 5 cm in the cross-machine direction and extends substantially continuously in the machine direction of said film.

4. The breathable film of claim 1 wherein the first region has a WVTR in excess of 1500 g/m$^2$/24 hours and further wherein said second region comprises from about 5% to about 75% of the area of said film.

5. The breathable film of claim 4 wherein said second region has a thickness less than said first region and wherein both said first and second regions extend adjacent each other in the machine direction.

6. The breathable film of claim 4 wherein said second region is substantially surrounded by said first region.

7. The breathable film of claim 6 wherein said second region is disposed at a central portion of said film.

8. The breathable film of claim 1 wherein said second region has a thickness less than the thickness of said first region and a WVTR at least about 25% less than the WVTR of said first region and further wherein said film has a basis weight less than about 35 g/m$^2$.

9. The breathable film of claim 8 wherein said film further comprises third region, said third region having a WVTR and thickness intermediate to that of said first and second regions and wherein said third region is contiguous with said second region.

10. The breathable film of claim 1 wherein said second region has a thickness less than 95% of the thickness of said first region and comprises from about 5% to about 75% of the area of said film.

11. A breathable film of claim 1 wherein said film comprises a polyolefin polymer and a filler and wherein said second region is thinner than said first region and has a decreased porosity level relative to said first region.

12. The polyolefin film of claim 11 wherein said first and second regions have a basis weight less than about 35 g/m$^2$ and wherein said second region has a thickness of less than about 90% of the thickness of said first region.

13. The film of claim 12 wherein said second region comprises from about 5% to about 75% of the surface area of said film.

14. The film of claim 13 wherein said second region extends in the machine direction adjacent said first region.

15. A multilayer film comprising:
   a first layer and a second layer, said first layer comprising a film having a first and second side and a WVTR in excess of about 800 g/m$^2$/24 hours; a second layer substantially continuously joined to the first side of said first layer, said second layer of the multilayer film comprising the film of claim 1.

16. The multilayer film of claim 15 wherein said first layer of said multilayer film comprises a monolithic, non-porous film and wherein said second layer comprises at least 10% of the total thickness of the multilayer film.

17. The multilayer film of claim 15 wherein said first layer of the multilayer film comprises a thermoplastic polymer microporous film and further wherein said second layer comprises a thermoplastic polymer which is heat sensitive relative to said thermoplastic polymer of said first layer and further wherein said second layer comprises at least 10% of the total thickness of the multilayer film.

18. The multilayer film of claim 15 wherein said first layer of said multilayer film comprises a microporous thermoplastic polymer film and wherein said second layer comprises a thermoplastic polymer having a softening point at least 20° C. below the softening point of the thermoplastic polymer comprising said first layer.

19. The multilayer film of claim 18 wherein said first and second regions of said second layer extend adjacent each other in the machine direction.

20. The multilayer film of claim 19 wherein said second region of said multilayer film overlays between 5% and about 75% of the surface area of the first side of said first layer.

21. The multilayer film of claim 15 wherein said first layer comprises a microporous heat stable polyolefin polymer film having a WVTR of at least 1500 g/m$^2$/24 hours and wherein said second layer comprises a heat sensitive thermoplastic polymer; and further wherein said second layer comprising at least 10% of the total thickness of said film.

22. The multilayer film of claim 21 wherein said first layer comprises a filled microporous film and said second layer comprises a filled microporous film and further wherein said heat sensitive polymer has a softening point at least about 20° C. less than said heat stable polyolefin polymer.

23. The multilayer film of claim 22 wherein said first microporous polyolefin layer comprises linear low density polyethylene polymer and wherein said second layer comprises a polymer having a softening point less than about 98° C.

24. The multilayer film of claim 23 wherein both of said first and second region of the second layer extend adjacent one another in the machine direction and wherein said second region of said second layer overlays from 5% to about 75% of the first side of said first layer.

* * * * *